United States Patent
Young et al.

(10) Patent No.: US 6,627,183 B1
(45) Date of Patent: *Sep. 30, 2003

(54) HAIR CARE COMPOSITIONS

(75) Inventors: Wendy Victoria Jane Young, Newbury (GB); Graham Neil McKelvey, Woking (GB); Chantelle Mary McCann, Egham (GB); Anthony McMeekin, Chertsey (GB)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/744,833
(22) PCT Filed: Mar. 26, 1999
(86) PCT No.: PCT/US99/06114
§ 371 (c)(1), (2), (4) Date: Jan. 18, 2002
(87) PCT Pub. No.: WO00/06102
PCT Pub. Date: Feb. 10, 2000

(30) Foreign Application Priority Data

Jul. 30, 1998 (WO) .............................. PCT/US98/15749

(51) Int. Cl.[7] .......................... A61K 7/06; A61K 7/075; A61K 7/00; A61K 7/08; A61K 31/174
(52) U.S. Cl. ................ 424/70.1; 424/70.27; 424/78.02; 424/78.08; 424/400; 424/401
(58) Field of Search .............................. 424/70.1, 70.27, 424/78.02, 78.08, 400, 401

(56) References Cited

U.S. PATENT DOCUMENTS 5,100,657 A * 3/1992 Ansher-Jackson et al. . 424/70.1
5,470,551 A    11/1995 Dubief et al.

FOREIGN PATENT DOCUMENTS

| DE | 4326866 | 2/1995 |
|---|---|---|
| EP | 0 240 350 | 6/1995 |
| EP | 0 774247 | 5/1997 |
| EP | 0 796611 | 9/1997 |
| GB | 2211192 | 6/1989 |
| GB | 2297757 | 8/1996 |
| JP | 54-138133 | 10/1979 |
| WO | WO 92/16187 | 10/1992 |
| WO | WO 94/08557 | 4/1994 |
| WO | WO 97/07782 | 3/1997 |
| WO | WO 97/35542 | 10/1997 |
| WO | WO 97/35545 | 10/1997 |
| WO | WO 97/35546 | 10/1997 |
| WO | WO 97/35549 | 10/1997 |
| WO | WO 98/18434 | 5/1998 |
| WO | WO 98/19654 | 5/1998 |
| WO | WO 98/29094 | 7/1998 |
| WO | WO-00/06102 | 2/2000 |
| WO | WO-00/06105 | 2/2000 |
| WO | WO-00/06107 | 2/2000 |

* cited by examiner

*Primary Examiner*—Shelley A. Dodson
(74) *Attorney, Agent, or Firm*—Brahm J. Corstange; Linda M. Sivik

(57) ABSTRACT

According to the present invention there is provided a hair care composition comprising: (a) cationic saccharide polymer or copolymer wherein the cationic polymer has a charge density of greater than about 1.5 meq/g, preferably greater than about 1.6 meq/g, more preferably greater than about 1.7 meq/g, even more preferably greater than about 1.8 meq/g; and (b) less than about 5%, preferably less than about 2%, more preferably less than about 1%, even more preferably 0%, by weight, of anionic surfactant. The compositions of the present invention provide good conditioning/shine to the hair with reduced feelings of tackiness and greasiness.

26 Claims, No Drawings

HAIR CARE COMPOSITIONS

The present invention relates to hair care compositions. In particular, it relates to hair care compositions which give good conditioning/shine to the hair with reduced feelings of tackiness and greasiness.

BACKGROUND TO THE INVENTION

Hair is often subjected to a wide variety of insults that can cause damage. These include shampooing, rinsing, drying, heating, combing, styling, perming, colouring, exposure to the elements etc. Thus the hair is often in a dry, rough, lusterless or frizzy condition due to abrasion of the hair surface and removal of the hair's natural oils and other natural conditioning and moisturizing components.

A variety of approaches have been developed to alleviate these conditions. These include the use of ultra mild shampoo compositions, the use of hair conditioning shampoos which attempt to both cleanse and condition the hair from a single product and the use of hair conditioning formulations such as rinse-off and leave-on products.

Leave-on hair care formulations provide added advantages over the other approaches. For example, leave-on formulations are more cost effective and work for a longer duration because the conditioning ingredients remain on the hair. They are more convenient because the consumer can use the product at any time and does not have to wait to rinse the product. Also, the product may be applied to the parts of the hair most in need of the conditioning benefits.

Cationic polysaccharides are well known in the art for providing conditioning benefits. See, for example, WO-A-97/35542, WO-A-97/35545, WO-A-97/35546, all of which describe the use of cationic polysaccharides in conditioning shampoo compositions. GB-A-2,211,192 describes the use of cationic polysaccharides in a rinse-off conditioning composition. DE-A-4,326,866 describes a composition for use prior to cutting of the hair that comprises a cationic polysaccharide. JP-54 138 133 describes hair product compositions containing polypeptides and cationic celluloses. However, these cationic polysaccharides are also known to cause stickiness or tackiness. This can lead to the consumer feeling the hair is dirty or greasy, especially with leave-on conditioning compositions where there is no rinsing step.

It has now been surprisingly found that cationic saccharide polymers and copolymers having a cationic charge density of greater than 1.5 meq/g provide improved shine/conditioning benefits to the hair with reduced tackiness and greasiness.

While not wishing to be bound by theory, it is believed that the high cationic charge density makes the polymer more substantive to the hair providing good conditioning benefits. The cationic groups interact with the negative charge on the hair. Binding sites occur more frequently due to the increased frequency of said cationic groups along the polymer. The more frequent interactions may 'pull' the polymer backbone into closer association with the hair fibre thus reducing the depth of the hydrocarbon layer and reducing its tendency to interact with other surfaces such as skin on the fingers. Hence, there is a reduced feeling of tackiness and, due to the close association of polymer and hair, an enhanced shine.

SUMMARY OF THE INVENTION

According to the present invention there is provided a hair care composition comprising:
(a) cationic saccharide polymer or copolymer wherein the cationic polymer has a charge density of greater than about 1.5 meq/g, preferably greater than about 1.6 meq/g, more preferably greater than about 1.7 meq/g, even more preferably greater than about 1.8 meq/g; and
(b) less than about 5%, preferably less than about 2%, more preferably less than about 1%, even more preferably 0%, by weight, of anionic surfactant.

The compositions of the present invention have reduced tackiness and greasiness while delivering good conditioning/shine benefits.

All concentrations and ratios herein are by weight of the hair care composition, unless otherwise specified.

All averages are weight averages unless otherwise specified.

DETAILED DESCRIPTION OF THE INVENTION

The hair care compositions of the present invention comprise two main elements, cationic polymers or copolymers of saccharides and less than 5% anionic surfactant. These elements will be described in more detail below.

As used herein the terms "tacky" and "tackiness" means the adhesive feeling of the hair after the application of some hair care compositions.

As used herein the term "leave-on" means a hair care composition that is intended to be used without a rinsing step. Therefore, leave-on compositions will generally be left on the hair until the consumer next washes their hair as part of their cleansing regimen. Leave-on will generally comprise less than about 5% of anionic surfactant and will generally comprise less than 5% of non-ionic surfactant.

Cationic Polymers or Copolymers of Saccharides

An essential feature of the compositions of the present invention is that they comprise a cationic polymer or copolymer of saccharide. The cationic saccharides of the present compositions have a cationic charge density of greater than about 1.5 meq/g, preferably greater than about 1.6 meq/g, more preferably greater than about 1.7 meq/g, even more preferably greater than about 1.8 meq/g. Generally the cationic polymers will have a cationic charge density of less than about 5 meq/g, preferably less than about 3.5 meq/g, more preferably less than about 2.5 meq/g, even more preferably less than about 2.2 meq/g.

The "cationic charge density" of a polymer refers to the ratio of the number of positive charges on a monomeric unit of which the polymer is comprised to the molecular weight of said monomeric unit, i.e.:

$$\text{Cationic Charge Density} = \frac{\text{number of positive charges}}{\text{monomeric unit molecular weight}}$$

The cationic charge density of the cationic polymers herein can be determined using the Kjeldahl Method (United States Pharmacopoeia—Chemical tests—<461> Nitrogen Determination—method II). Those skilled in the art will recognise that the charge density of some of the polymers herein may vary depending upon pH and the isoelectric point of the cationic charge groups. The charge density should be within the above limits at the pH of intended use.

The cationic saccharides of the present invention generally comprise from about 1% to about 10%, preferably from about 2% to about 5%, more preferably from about 2.3% to about 3%, even more preferably from about 2.5% to about 2.9%, by weight, of cationic nitrogen.

The concentration of the cationic saccharide should be sufficient to provide the desired conditioning benefits. Such concentrations generally range from about 0.001% to about 20%, preferably from about 0.005% to about 10%, more preferably from about 0.01% to about 2%, even more preferably from about 0.05% to about 1%, by weight, of the total composition.

The cationic saccharides for use herein will generally have an average molecular weight of from about 5000 to about 10 million, preferably from about 100,000 to about 5 million, more preferably from about 500,000 to about 2 million, even more preferably from about 1 million to about 1.5 million.

Suitable cationic saccharides for use in the present invention include cationic polysaccharides and cationic copolymers of saccharides, preferred are cationic polysaccharides.

The cationic polymers for use herein are cationic polymers and copolymers of saccharides. The cationic polysaccharides useful in the present invention include those polymers based on 5 or 6 carbon sugars and derivatives which have been made water-soluble by, for example, derivatising them with ethylene oxide. These polymers may be bonded via any of several arrangements, such as 1,4-α, 1,4-β, 1,3-α, 1,3-β and 1,6 linkages. The monomers may be in straight chain or branched chain geometric arrangements.

Suitable non-limiting examples of cationic polysaccharides include those based on the following: celluloses and hydroxyalkylcelluloses; starches and hydroxyalkylstarches; polymers based on arabinose monomers; polymers derived from xylose monomers; polymers derived from fucose monomers; polymers derived from fructose monomers; polymers based on acid-containing sugar monomers such as galacturonic acid and glucuronic acid; polymers based on amine sugar monomers such as galactosamine and glucosamine, particularly acetylglucosamine; polymers based on 5 or 6 membered ring polyalcohol monomers; polymers based on galactose monomers; polymers based on mannose monomers and polymers based on galactomannan monomers.

Preferred for providing shine and conditioning benefits to the hair with reduced tack and greasiness are cationic polymers based on cellulose, hyroxyalkylcellulose, acetylglucosamine and derivatives. More preferred are cationic polymers based on hydroxyalkylcelluloses, especially hydroxyethylcellulose. Non-limiting examples of suitable cationic polymers are those available from Amerchol Corp. (Edison, N.J., USA) as salts of hydroxyethyl cellulose reacted with trimethyl ammonium substituted epoxide, referred to in the industry (CTFA) as Polyquaternium 10. Background material on these polymers and their manufacture, can be found in U.S. Pat. No. 3,472,840 (issued Oct. 14, 1969 to Stone), herein incorporated by reference. Other types of cationic cellulose include the polymeric quaternary ammonium salts of hydroxyethyl cellulose reacted with lauryl dimethyl ammonium-substituted epoxide, referred to in the industry (CTFA) as Polyquatemium 24, available from Amerchol Corp. (Edison, N.J., USA) and polymeric quaternary ammonium salts of hydroxyethyl cellulose reacted with diallyl dimethyl ammonium chloride, referred to in the industry (CTFA) as Polyquaternium 4, available from National Starch (Salisbury, N.C., USA).

The cationic copolymers of saccharides useful in the present invention encompass those containing the following saccharide monomers and their derivatives: glucose, galactose, mannose, arabinose, xylose, fucose, fructose, glucosamine, galactosamine, glucuronic acid, galacturonic acid, and 5 or 6 membered ring polyalcohols. Also included are hydroxymethyl, hydroxyethyl and hydroxypropyl derivatives of the above sugars. When saccharides are bonded to each other in the copolymers, they may be bonded via any of several arrangements, such as 1,4-α, 1,4-β, 1,3-α, 1,3-β and 1,6 linkages. Any other monomers can be used as long as the resultant polymer is suitable for use in hair care. Non-limiting examples of other monomers useful herein include dimethyldiallylammonium chloride, dimethylaminoethylmethyl acrylate, diethyldiallylammonium chloride, N,N-diallyl,N-N-dialkyl ammonium halides, and the like.

Anionic Surfactant

A second essential feature of the compositions of the present invention is that they comprise less than about 5%, preferably less than about 4%, more preferably. less than about 2%, even more preferably less than about 1%, even more preferably still 0%, by weight, of an anionic surfactant. As used herein, "anionic surfactant" means anionic surfactants and zwitterionic or amphoteric surfactants which have an attached group that is anionic at the pH of the composition, or a combination thereof.

Examples of anionic surfactants are alkyl sulphates and alkyl ether sulphates. These materials have the respective formulae $ROSO_3M$ and $RO(C_2H_4O)_xSO_3M$, wherein R is an alkyl or alkenyl group of from about 8 to about 18 carbon atoms, x is an integer having a value of from 1 to 10 and M is a cation such as ammonium, alkanolamines such as triethanolamine, monovalent metals such as sodium and potassium and polyvalent metal cations such as magnesium and calcium.

Other examples of anionic surfactants are the water-soluble salts of organic, sulphuric acid reactions products conforming to the formula $[R^1—SO_3—M]$ where $R^1$ is a straight or a branched chain, saturated, aliphatic hydrocarbon radical having from about 8 to about 24 carbon atoms and M is a cation as described hereinabove.

Still other examples of anionic surfactants are the reaction products of fatty acids esterified with isoethionic acid and neutralised with sodium hydroxide where, for example, the fatty acids are derived from coconut oil or palm kernel oil, sodium or potassium salts of fatty acid amides of methyl tauride in which the fatty acids, for example, are derived from coconut oil or palm kernel oil.

Further examples of anionic surfactants are the succinates, examples of which include disodium N-octadecylsulphosuccinate, disodium lauryl sulphosuccinate, diammonium lauryl sulphosuccinate, diamyl ester of sodium sulphosuccinic acid, dihexyl ester of sodium sulphosuccinic acid and dioctyl ester of sodium sulphosuccinic acid.

Still further examples of anionic surfactants includes olefin sulphonates having from about 10 to about 24 carbon atoms. In this context, the term "olefin sulphonate" refers to compounds which can be produced by the sulphonation of α-olefins by means of uncomplexed sulphur trioxide, followed by neutralisation of the acid reaction mixture in conditions such that any sulphones which have formed in the reaction are hydrolysed to give the corresponding hydroxy-alkanesulphonates.

Another class of anionic surfactants are the β-alkyloxy sulphonates. These surfactants conform to the formula

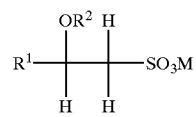

where R1 is a straight chain alkyl group having from about 6 to about 20 carbon atoms, R2 is a lower alkyl group having from about 1 to about 3 carbon atoms and M is a water-soluble cation as described hereinabove.

Optional Ingredients

The hair care compositions of the present invention can further comprise a number of optional ingredients. Some non-limiting examples of these optional ingredients are given below.

Silicone Conditioning Agent

The compositions of the present invention may optionally include a silicone conditioning component. The silicone conditioning component may comprise volatile silicone, nonvolatile silicone, or mixtures thereof. As used herein, "nonvolatile" refers to silicone material with little or no significant vapour pressure under ambient conditions, as is understood by those in the art. Boiling point under one atmosphere (atm) will preferably be at least about 250° C., more preferably at least about 275° C., most preferably at least about 300° C. Vapour pressure is preferably about 0.2 mm Hg at 25° C. or less, preferably about 0.1 mm Hg at 25° C. or less.

The silicone conditioning component for use herein can be a silicone fluid, a silicone gums, silicone resins and mixtures thereof. References disclosing non-limiting examples of some suitable silicone hair conditioning agents, and optional suspending agents for the silicone, are described in WO-A-94/08557 (Brock et al.), U.S. Pat. No. 5,756,436 (Royce et al.), U.S. Pat. No. 5,104,646 (Bolich Jr. et al.), U.S. Pat. No. 5,106,609 (Bolich Jr. et al.) and U.S. Reissue 34,584 (Grote et al.) British Patent 849,433, all of which are incorporated herein by reference.

Silicone resins are highly cross-linked siloxane systems where the crosslinking is introduced through the incorporation of trifunctional and tetrafunctional silanes with monofunctional or difunctional, or both, silanes during manufacture of the silicone resin. As is well understood in the art, the degree of crosslinking that is required in order to result in a silicone resin will vary according to the specific silane units incorporated into the silicone resin. In general, silicone materials which have a sufficient level of trifunctional and tetrafunctional siloxane monomer units (and hence, a sufficient level of crosslinking) such that they dry down to a rigid, or hard, film are considered to be silicone resins. The ratio of oxygen atoms to silicon atoms is indicative of the level of crosslinking in a particular silicone material. Silicone materials which have at least about 1.1 oxygen atoms per silicon atom will generally be silicone resins herein. Preferably, the ratio of oxygen:silicon atoms is at least about 1.2:1.0. Silanes used in the manufacture of silicone resins include monomethyl, dimethyl, trimethyl, monophenyl, diphenyl, methylphenyl, ethylphenyl, propylphenyl, monovinyl, and methylvinylchlorosilanes, and tetrachlorosilane.

If present, the silicone resin will generally comprise from about 0.001% to about 10%, preferably from about 0.005% to about 5%, more preferably from about 0.01% to about 2%, even more preferably from about 0.1% to about 1%, by weight, of the total composition.

Any polysiloxane resin suitable for use in hair care compositions may be used herein including those possessing hydrogen, hydroxy, alkyl, aryl, alkoxy, alkaryl, arylalkyl arylalkoxy, alkaryloxy and alkamino substituents. However, preferred polysiloxane resins have at least one substituent group possessing delocalised electrons. This substituent can be selected from alkyl, aryl, alkoxy, alkaryl, arylalkyl arylalkoxy, alkaryloxy, and combinations thereof. Preferred are aryl, arylalkyl and alkaryl substituents. More preferred are alkaryl and arylalkyl substituents. Evan more preferred are alkaryl substituents, particularly 2-phenyl propyl. Whereas it is preferred that at least one substituent have delocalised electrons, the resins herein will also generally have other substituents without delocalised electrons. Such other substituents can include hydrogen, hydroxyl, alkyl, alkoxy, amino functionalities and mixtures thereof. Preferred are alkyl substituents, especially methyl substituents.

As used herein the term "aryl" means a functionality containing one or more homocyclic or heterocyclic rings. The aryl functionalities herein can be unsubstituted or substituted and generally contain from 3 to 16 carbon atoms. Preferred aryl groups include, but are not limited to, phenyl, naphthyl, cyclopentadienyl, anthracyl, pyrene, pyridine, pyrimidine As used herein the term "alkyl" means a saturated or unsaturated, substituted or unsubstituted, straight or branched-chain, hydrocarbon having from 1 to 10 carbon atoms, preferably 1 to 4 carbon atoms. The term "alkyl" therefore includes alkenyls having from 2 to 8, preferably 2 to 4, carbons and alkynyls having from 2 to 8, preferably 2 to 4, carbons. Preferred alkyl groups include, but are not limited to, methyl, ethyl, propyl, isopropyl, and butyl. More preferred are methyl, ethyl and propyl.

As used herein the term "alkaryl" means a substituent comprising an alkyl moiety and an aryl moiety wherein the alkyl moiety is bonded to the siloxane resin.

As used herein the term "arylalkyl" means a substituent comprising an aryl moiety and an alkyl moiety wherein the aryl moiety is bonded to the siloxane resin.

Silicone materials and silicone resins in particular, can conveniently be identified according to a shorthand nomenclature system well known to those skilled in the art as "MDTQ" nomenclature. Under this system, the silicone is described according to presence of various siloxane monomer units which make up the silicone. Briefly, the symbol M denotes the monofunctional unit $(CH_3)_3SiO_{0.5}$; D denotes the difunctional unit $(CH_3)_2SiO$; T denotes the trifunctional unit $(CH_3)SiO_{1.5}$; and Q denotes the quadri- or tetra-functional unit $SiO_2$. Primes of the unit symbols, e.g., M', D', T', and Q' denote siloxane units with one or more substituents other than methyl, and must be specifically defined for each occurrence. Therefore, the preferred polysiloxane resins for use herein have at least one M', D', T' or Q' functionality that possesses a substituent group with delocalised electrons. Preferred substituents are as defined hereinabove. The molar ratios of the various units, either in terms of subscripts to the symbols indicating the total number of each type of unit in the silicone (or an average thereof) or as specifically indicated ratios in combination with molecular weight complete the description of the silicone material under the MDTQ system.

Preferred polysiloxane resins for use herein are MQ and M'Q resins, more preferred are M'Q resins especially $M'_6Q_3$, $M'_8Q_4$, $M'_{10}Q_5$, $M'_{12}Q_6$ resins and mixture thereof. Preferred M'Q resins are those which have at least one group containing delocalised electrons substituted on each M' functionality. More preferred are resins where the other substituent groups are alkyl, especially methyl.

The polysiloxane resins for use herein will preferably have a viscosity of less than about 5000 $mm^2s^{-1}$, more preferably less than about 2000 $mm^2s^{-1}$, even more preferably less than about 1000 $mm^2s^{-1}$, even more still preferably less than about 600 $mm^2s^{-1}$, at 25° C. The viscosity can be measured by means of a Cannon-Fenske Routine Viscometer (ASTM D-445).

Background material on polysiloxane resins suitable for use herein, including details of their manufacture, can be found in U.S. Pat. Nos. 5,539,137; 5,672,338; 5,686,547 and 5,684,112, all of which are incorporated herein by reference.

Silicone fluids for use in the present compositions include silicone oils which are flowable silicone materials with a viscosity of less than 1,000,000 mm$^2$s$^{-1}$, preferably between about 5 and 1,000,000 mm$^2$s$^{-1}$, more preferably between about 10 and about 600,000 mm$^2$s$^{-1}$, more preferably between about 10 and about 500,000 mm$^2$s$^{-1}$, most preferably between 10 and 350,000 mm$^2$s$^{-1}$ at 25° C. The viscosity can be measured by means of a glass capillary viscometer as set forth in Dow Corning Corporate Test Method CTM0004, Jul. 20, 1970. Suitable silicone oils include polyalkyl siloxanes, polyaryl siloxanes, polyarylalkyl siloxanes, polyalkaryl siloxanes, polyether siloxane copolymers, and mixtures thereof. Other insoluble, nonvolatile silicone fluids having conditioning properties can also be used.

Silicone oils for use in the composition include polyalkyl or polyaryl siloxanes which conform to following formula:

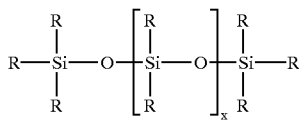

where R is aliphatic, preferably alkyl or alkenyl, or aryl, R can be substituted or unsubstituted, and x is an integer from 1 to about 8,000. Suitable unsubstituted R groups include alkoxy, aryloxy, alkaryl, arylalkyl, alkamino, and ether-substituted, hydroxyl-substituted, and halogen-substituted aliphatic and aryl groups. Suitable R groups also include cationic amines and quaternary ammonium groups.

The aliphatic or aryl groups substituted on the siloxane chain may have any structure as long as the resulting silicones remain fluid at room temperature, are hydrophobic, are neither irritating, toxic nor otherwise harmful when applied to the hair, are compatible with the other components of the herein described hair care compositions, are chemically stable under normal use and storage conditions, are insoluble in the compositions of the present invention and are capable of conditioning the hair.

The two R groups on the silicon atom of each monomeric silicone unit may represent the same group or different groups. Preferably, the two R groups represent the same group.

Preferred alkyl and alkenyl substituents are $C_1$–$C_5$ alkyls and alkenyls, more preferably from $C_1$–$C_4$, most preferably from $C_1$–$C_2$. The aliphatic portions of other alkyl-, alkenyl-, or alkynyl-containing groups (such as alkoxy, alkaryl, and alkamino) can be straight or branched chains and preferably have from one to five carbon atoms, more preferably from one to four carbon atoms, even more preferably from one to three carbon atoms, most preferably from one to two carbon atoms. As discussed above, the R substituents hereof can also contain amino functionalities, e.g. alkamino groups, which can be primary, secondary or tertiary amines or quaternary ammonium. These include mono-, di- and tri-alkylamino and alkoxyamino groups wherein the aliphatic portion chain length is preferably as described above. The R substituents can also be substituted with other groups, such as halogens (e.g. chloride, fluoride, and bromide), halogenated aliphatic or aryl groups, and hydroxy (e.g. hydroxy substituted aliphatic groups). Suitable halogenated R groups could include, for example, tri-halogenated (preferably fluoro) alkyl groups such as —$R^1$—$C(F)_3$, wherein $R^1$ is $C_1$–$C_3$ alkyl. Examples of such polysiloxanes include polymethyl-3,3,3 trifluoropropylsiloxane.

Suitable R groups include methyl, ethyl, propyl, phenyl, methylphenyl and phenylmethyl. The preferred silicones are polydimethyl siloxane, polydiethylsiloxane, and polymethylphenylsiloxane. Polydimethylsiloxane is especially preferred. Other suitable R groups include methyl, methoxy, ethoxy, propoxy, and aryloxy. The three R groups on the end caps of the silicone may also represent the same or different groups.

The nonvolatile polyalkylsiloxane fluids that may be used include, for example, polydimethylsiloxanes. These siloxanes are available, for example, from the General Electric Company in their Viscasil R and SF 96 series, and from Dow Corning in their Dow Corning 200 series.

The polyalkylaryl siloxane fluids that may be used, also include, for example, polymethylphenylsiloxanes. These siloxanes are available, for example, from the General Electric Company as SF 1075 methyl phenyl fluid or from Dow Corning as 556 Cosmetic Grade Fluid.

The polyether siloxane copolymers that may be used include, for example, a polypropylene oxide modified polydimethylsiloxane (e.g., Dow Corning DC-1248) although ethylene oxide or mixtures of ethylene oxide and propylene oxide may also be used. For insoluble silicones the ethylene oxide and polypropylene oxide level must be sufficiently low to prevent solubility in water and the composition hereof.

Other suitable silicone fluids for use in the silicone conditioning agents are insoluble silicone gums. These gums are polyorganosiloxane materials having a viscosity at 25° C. of greater than or equal to 1,000,000 centistokes. Silicone gums are described in U.S. Pat. No. 4,152,416; Noll and Walter, *Chemistry and Technology of Silicones*, New York: Academic Press 1968; and in General Electric Silicone Rubber Product Data Sheets SE 30, SE 33, SE 54 and SE 76, all of which are incorporated herein by reference. The silicone gums will typically have a mass molecular weight in excess of about 200,000, generally between about 200,000 and about 1,000,000, specific examples of which include polydimethylsiloxane, (polydimethylsiloxane)(methylvinylsiloxane) copolymer, poly(dimethylsiloxane) (diphenyl siloxane)(methylvinylsiloxane) copolymer and mixtures thereof.

The silicone conditioning agent can also comprise a mixture of polydimethylsiloxane gum (viscosity greater than about 1,000,000 centistokes) and polydimethylsiloxane oil (viscosity from about 10 to about 100,000 centistokes), wherein the ratio of gum to fluid is from about 30:70 to about 70:30, preferably from about 40:60 to about 60:40.

The number average particle size of the optional silicone component can vary widely without limitation and will depend on the formulation and/or the desired characteristics. Number average particle sizes preferred for use in the present invention will typically range from about 10 nanometres to about 100 microns, more preferably from about 30 nanometres to about 20 microns.

Background material on silicones including sections discussing silicone fluids, gums, and resins, as well as manufacture of silicones, can be found in *Encyclopaedia of Polymer Science and Engineering* (Volume 15, Second Edition, pp. 204–308, John Wiley & Sons, Incorporated, 1989), incorporated herein by reference.

A preferred silicone conditioning agent from the viewpoint of improving shine is a silicone resin.

Cationic Conditioning Agents

The compositions of the present invention can also comprise one or more additional cationic polymeric conditioning agents. The cationic polymer conditioning agents will preferably be water soluble. The total level of cationic polymers in the compositions of the present invention is typically from about 0.001% to about 20%, more typically from about 0.005% to about 10%, preferably from about 0.01% to about 2%, by weight.

By "water soluble" cationic polymer, what is meant is a polymer which is sufficiently soluble in water to form a substantially clear solution to the naked eye at a concentration of 0.1% in water (distilled or equivalent) at 25° C. Preferably, the polymer will be sufficiently soluble to form a substantially clear solution at 0.5% concentration, more preferably at 1.0% concentration.

As used herein, the term "polymer" shall include materials whether made by polymerization of one type of monomer or made by two (i.e., copolymers) or more types of monomers.

The cationic polymers hereof will generally have a weight average molecular weight which is at least about 5,000, typically at least about 10,000, and is less than about 10 million. Preferably, the molecular weight is from about 100,000 to about 2 million. The cationic polymers will generally have cationic nitrogen-containing moieties such as quaternary ammonium or cationic amino moieties, and mixtures thereof.

The cationic charge density will be preferably at least about 0.1 meq/g, more preferably at least about 0.5 meq/g, even more preferably at least about 1.1 meq/g, most preferably at least about 1.2 meq/g. Generally, for practical purposes, the cationic polymers will have a cationic charge density of less than about 7 meq/g, preferably less than about 5 meq/g, more preferably less than about 3.5 meq/g, even more preferably less than about 2.5 meq/g. Cationic charge density of the cationic polymer can be determined using the Kjeldahl Method (United States Pharmacopoeia—Chemical tests—<461> Nitrogen Determination—method II). Those skilled in the art will recognise that the charge density of amino-containing polymers may vary depending upon pH and the isoelectric point of the amino groups. The charge density should be within the above limits at the pH of intended use.

Any anionic counterions can be utilized for the cationic polymers so long as the water solubility criteria is met. Suitable counterions include halides (e.g., Cl, Br, I, or F, preferably Cl, Br, or I), sulfate, and methylsulfate. Others can also be used, as this list is not exclusive.

The cationic nitrogen-containing moiety will be present generally as a substituent, on a fraction of the total monomer units of the cationic hair conditioning polymers.

Thus, the cationic polymer can comprise copolymers, terpolymers, etc. of quaternary ammonium or cationic amine-substituted monomer units and other non-cationic units referred to herein as spacer monomer units. Such polymers are known in the art, and a variety can be found in the *CTFA International Cosmetic Ingredient Dictionary and Handbook*, 7th edition, edited by Wenninger and McEwen, (The Cosmetic, Toiletry, and Fragrance Association, Inc., Washington, D.C., 1997).

Suitable cationic polymers include, for example, copolymers of vinyl monomers having cationic amine or quaternary ammonium functionalities with water soluble spacer monomers such as acrylamide, methacrylamide, alkyl and dialkyl acrylamides, alkyl and dialkyl methacrylamides, alkyl acrylate, alkyl methacrylate, vinyl caprolactone, and vinyl pyrrolidone. The alkyl and dialkyl substituted monomers preferably have $C_1$–$C_7$ alkyl groups, more preferably $C_1$–$C_3$ alkyl groups. Other suitable spacer monomers include vinyl esters, vinyl alcohol (made by hydrolysis of polyvinyl acetate), maleic anhydride, propylene glycol, and ethylene glycol.

The cationic amines can be primary, secondary, or tertiary amines, depending upon the particular species and the pH of the composition. In general, secondary and tertiary amines, especially tertiary amines, are preferred.

Amine-substituted vinyl monomers can be polymerised in the amine form, and then optionally can be converted to ammonium by a quaternization reaction. Amines can also be similarly quaternized subsequent to formation of the polymer. For example, tertiary amine functionalities can be quaternized by reaction with a salt of the formula R'X wherein R' is a short chain alkyl, preferably a $C_1$–$C_7$ alkyl, more preferably a $C_1$–$C_3$ alkyl, and X is an anion which forms a water soluble salt with the quaternized ammonium.

Suitable cationic amino and quaternary ammonium monomers include, for example, vinyl compounds substituted with dialkylaminoalkyl acrylate, dialkylaminoalkyl methacrylate, monoalkylaminoalkyl acrylate, monoalkylaminoalkyl methacrylate, trialkyl methacryloxyalkyl ammonium salt, trialkyl acryloxyalkyl ammonium salt, diallyl quaternary ammonium salts, and vinyl quaternary ammonium monomers having cyclic cationic nitrogen-containing rings such as pyridinium, imidazolium, and quaternized pyrrolidone, e.g., alkyl vinyl imidazolium, alkyl vinyl pyridinium, alkyl vinyl pyrrolidone salts. The alkyl portions of these monomers are preferably lower alkyls such as the $C_1$–$C_3$ alkyls, more preferably $C_1$ and $C_2$ alkyls. Suitable amine-substituted vinyl monomers for use herein include dialkylaminoalkyl acrylate, dialkylaminoalkyl methacrylate, dialkylaminoalkyl acrylamide, and dialkylaminoalkyl methacrylamide, wherein the alkyl groups are preferably $C_1$–$C_7$ hydrocarbyls, more preferably $C_1$–$C_3$, alkyls.

The cationic polymers hereof can comprise mixtures of monomer units derived from amine- and/or quaternary ammonium-substituted monomer and/or compatible spacer monomers.

Suitable cationic hair conditioning polymers include, for example: copolymers of 1-vinyl-2-pyrrolidone and 1-vinyl-3-methylimidazolium salt (e.g., chloride salt) (referred to in the industry by the Cosmetic, Toiletry, and Fragrance Association, "CTFA", as Polyquaternium-16), such as those commercially available from BASF Wyandotte Corp. (Parsippany, N.J., USA) under the LUVIQUAT tradename (e.g., LUVIQUAT FC 370); copolymers of 1-vinyl-2-pyrrolidone and dimethylaminoethyl methacrylate (referred to in the industry by CTFA as Polyquaternium-11) such as those commercially available from Gaf Corporation (Wayne, N.J., USA) under the GAFQUAT tradename (e.g., GAFQUAT 755N); cationic diallyl quaternary ammonium-containing polymers, including, for example, dimethyldiallylammonium chloride homopolymer and copolymers of acrylamide and dimethyldiallylammonium chloride, referred to in the industry (CTFA) as Polyquaternium 6 and Polyquaternium 7, respectively; and mineral acid salts of amino-alkyl esters of homo- and co-polymers of unsaturated carboxylic acids having from 3 to 5 carbon atoms, as described in U.S. Pat. No. 4,009,256, incorporated herein by reference.

As discussed above, the cationic polymer hereof is water soluble. This does not mean, however, that it must be soluble in the composition. Preferably however, the cationic polymer is either soluble in the composition, or in a complex coacervate phase in the composition formed by the cationic polymer and anionic material. Complex coacervates of the cationic polymer can be formed with anionic surfactants or with anionic polymers that can optionally be added to the compositions hereof (e.g., sodium polystyrene sulfonate).

Sensates

The hair care compositions of the present invention may also comprise a sensate. As used herein the term "sensate" means a substance that, when applied to the skin, causes a perceived sensation of a change in conditions, for example, but not limited to, heating, cooling, refreshing and the like.

Sensates are preferably utilized at levels of from about 0.001% to about 10%, more preferably from about 0.005% to about 5%, even more preferably from about 0.01% to about 1%, by weight, of the total composition.

Any sensate suitable for use in hair care compositions may be used herein. A non-limiting, exemplary list of suitable sensates can be found in GB-B-1315626, GB-B-1404596 and GB-B-1411785, all incorporated by reference herein. Preferred sensates for use in the compositions herein are camphor, menthol, I-isopulegol, ethyl menthane carboxamide and trimethyl isopropyl butanamide.

$C_1$–$C_6$ Aliphatic Alcohols

The compositions of the present invention may optionally comprise $C_1$–$C_6$, preferably $C_2$–$C_3$, more preferably $C_2$ aliphatic alcohol. The aliphatic alcohol will generally comprise from about 1% to about 75%, preferably from about 10% to about 40%, more preferably from about 15% to about 30%, even more preferably from about 18% to about 26%, by weight, of the total composition.

Viscosity Modifier

The compositions of the present invention can also comprise viscosity modifiers. Any viscosity modifier suitable for use in hair care compositions may be used herein. Generally, if present, the viscosity modifier will comprise from about 0.01% to about 10%, preferably from about 0.05% to about 5%, more preferably from about 0.1% to about 3%, by weight, of the total composition. A non-limiting list of suitable viscosity modifiers can be found in the *CTFA International Cosmetic Ingredient Dictionary and Handbook,* 7th edition, edited by Wenninger and McEwen, (The Cosmetic, Toiletry, and Fragrance Association, Inc., Washington, D.C., 1997), herein incorporated by reference.

Suitable viscosity modifiers for use herein include shear sensitive viscosity modifiers. As used herein "shear sensitive viscosity modifiers" means viscosity modifiers that can form compositions whose viscosity decreases at low shear rates. Shear rate ($s^{-1}$) can be defined as the ratio of the velocity ($ms^{-1}$) of material to its distance from a stationary object (m). Shear rates of less than about $250s^{-1}$ can be thought of as "low shear rates". Any shear sensitive viscosity modifier suitable for use in hair care may be used herein However, preferred for use herein are viscosity modifiers which form compositions whose viscosity decreases at a shear rate of less than about $100s^{-1}$, more preferably less than about $50s^{-1}$. In addition, preferred shear sensitive viscosity modifiers are those which can form compositions whose viscosity decreases by more than about 30%, preferably more than about 50%, more preferably more than about 70%, even more preferably more than about 80% at a shear rate of $50s^{-1}$.

Preferred viscosity modifiers for use herein are those which form compositions whose viscosity is also sensitive to the electrolyte concentration in the aqueous phase, known hereafter as "salt sensitive viscosity modifiers". Background material on the properties of salt sensitive viscosity modifiers can be found in *American Chemical Society Symposium Series* (1991), Vol. 462, pp101–120, incorporated herein by reference. Any salt sensitive viscosity modifier suitable for use in hair care compositions may be used herein.

Examples of suitable viscosity modifiers include, but are not limited to, synthetic hectorites, carboxylic anionic polymers/copolymers and carboxylic anionic cross-linked polymers/copolymers. Preferred for use herein are carboxylic anionic cross-linked polymers and copolymers. More preferred are carboxylic anionic cross-linked copolymers.

The synthetic hectorites useful herein are synthetic layered silicates such as sodium-magnesium silicate. Examples of suitable synthetic hectorites include those available from Laporte Plc., United Kingdom under the trade name Laponite.

The carboxylic anionic copolymers useful herein can be hydrophobically-modified cross-linked copolymers of carboxylic acid and alkyl carboxylate, and have an amphiphilic property. These carboxylic anionic copolymers are obtained by copolymerising 1) a carboxylic acid monomer such as acrylic acid, methacrylic acid, maleic acid, maleic anhydride, itaconic acid, fumaric acid, crotonic acid, or α-chloroacrylic acid, 2) a carboxylic ester having an alkyl chain of from 1 to about 30 carbons, and preferably 3) a crosslinking agent of the following formula:

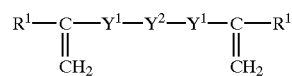

wherein $R^1$ is a hydrogen or an alkyl group having from about 1 to about 30 carbons; $Y^1$, independently, is oxygen, $CH_2O$, $COO$, $OCO$,

or

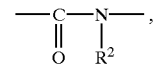

wherein $R^2$ is a hydrogen or an alkyl group having from about 1 to about 30 carbons; and $Y^2$ is selected from $(CH_2)_{m''}$, $(CH_2CH_2O)_{m''}$, or $(CH_2CH_2CH_2O)_{m''}$ wherein m" is an integer of from 1 to about 30.

Suitable carboxylic anionic copolymers herein are acrylic acid/alkyl acrylate copolymers having the following formula:

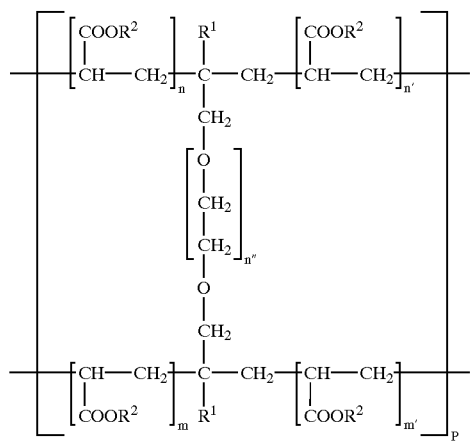

wherein $R^2$, independently, is a hydrogen or an alkyl of 1 to 30 carbons wherein at least one of $R^2$ is a hydrogen, $R^1$ is as defined above, n, n', m and m' are integers in which n+n'+m+m' is from about 40 to about 100, n" is an integer of from 1 to about 30, and P is defined so that the copolymer has a molecular weight of about 5000 to about 3,000,000.

Neutralizing agents may be included to neutralize the carboxylic anionic copolymers herein. Non-limiting examples of such neutralizing agents include sodium hydroxide, potassium hydroxide, ammonium hydroxide, monethanolamine, diethanolamine, triethanolamine, diisopropanolamine, aminomethylpropanol, tromethamine, tetrahydroxypropyl ethylenediamine, and mixtures thereof.

Non-limiting examples of suitable carboxylic anionic viscosity modifiers, including details of their manufacture, can be found in U.S. Pat. Nos. 3,940,351; 5,288,814; 5,349,030; 5,373,044 and 5,468,797, all of which are incorporated herein by reference. Examples of carboxylic anionic viscosity modifiers include those available from B. F. Goodrich, Cleveland, Ohio, USA under the trade names Pemulen TR-1, Pemulen TR-2, Carbopol 980, Carbopol 981, Carbopol ETD-2020, Carbopol ETD-2050 and Carbopol Ultrez 10. Preferred are Carbopol ETD-2020, Carbopol ETD-2050 and Carbopol Ultrez 10, especially Carbopol Ultrez 10.

Particularly preferred viscosity modifiers for use herein from the viewpoint of improving spreadability, reducing tack and improving shine are carboxylic anionic viscosity modifiers such as Carbopol Ultrez 10.

Polyethylene Glycol Derivatives of Glycerides

Suitable polyethylene glycol derivatives of glycerides include any polyethylene glycol derivative of glycerides which are water-soluble and which are suitable for use in a hair care composition. Suitable polyethylene glycol derivatives of glycerides for use herein include derivatives of mono-, di- and tri-glycerides and mixtures thereof.

One class of polyethylene glycol derivatives of glycerides suitable herein are those which conform to the general formula (I):

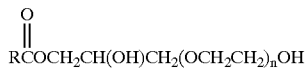

wherein n, the degree of ethoxylation, is from about 4 to about 200, preferably from about 5 to about 150, more preferably from about 20 to about 120, and wherein R comprises an aliphatic radical having from about 5 to about 25 carbon atoms, preferably from about 7 to about 20 carbon atoms.

Suitable polyethylene glycol derivatives of glycerides can be polyethylene glycol derivatives of hydrogenated castor oil. For example, PEG-20 hydrogenated castor oil, PEG-30 hydrogenated castor oil, PEG40 hydrogenated castor oil, PEG-45 hydrogenated castor oil, PEG-50 hydrogenated castor oil, PEG-54 hydrogenated castor oil, PEG-55 hydrogenated castor oil, PEG-60 hydrogenated castor oil, PEG-80 hydrogenated castor oil, and PEG-100 hydrogenated castor oil. Preferred for use in the compositions herein is PEG-60 hydrogenated castor oil.

Other suitable polyethylene glycol derivatives of glycerides can be polyethylene glycol derivatives of stearic acid. For example, PEG-30 stearate, PEG40 stearate, PEG-50 stearate, PEG-75 stearate, PEG-90 stearate, PEG-100 stearate, PEG-120 stearate, and PEG-150 stearate. Preferred for use in the compositions herein is PEG-100 stearate.

Cationic Surfactant

Cationic surfactants useful in compositions of the present invention, contain amino or quaternary ammonium moieties. The cationic surfactant will preferably, though not necessarily, be insoluble in the compositions hereof. Cationic surfactants among those useful herein are disclosed in the following documents, all incorporated by reference herein: M.C. Publishing Co., McCutcheon's, Detercients & Emulsifiers, (North American edition 1979); Schwartz, et al.; Surface Active Agents, Their Chemistry and Technoloqy, New York: Interscience Publishers, 1949; U.S. Pat. No. 3,155,591, Hilfer, issued Nov. 3, 1964; U.S. Pat. No. 3,929,678, Laughlin et al., issued Dec. 30, 1975; U.S. Pat. No. 3,959,461, Bailey et al., issued May 25, 1976; and U.S. Pat. No. 4,387,090, Bolich, Jr., issued Jun. 7, 1983.

Among the quaternary ammonium-containing cationic surfactant materials useful herein are those of the general formula:

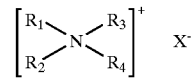

wherein $R_1$–$R_4$ are independently an aliphatic group of from about 1 to about 22 carbon atoms or an aromatic, alkoxy, polyoxyalkylene, alkylamido, hydroxyalkyl, aryl or alkylaryl group having from about 1 to about 22 carbon atoms; and X is a salt-forming anion such as those selected from halogen, (e.g. chloride, bromide), acetate, citrate, lactate, glycolate, phosphate nitrate, sulfate, and alkylsulfate radicals. The aliphatic groups may contain, in addition to carbon and hydrogen atoms, ether linkages, and other groups such as amino groups. The longer chain aliphatic groups, e.g., those of about 12 carbons, or higher, can be saturated or unsaturated. Especially preferred are mono-long chain (e.g., mono $C_{12}$–$C_{22}$, preferably $C_{12}$–$C_{18}$, more preferably $C_{16}$, aliphatic, preferably alkyl), di-short chain (e.g., $C_1$–$C_3$ alkyl, preferably $C_1$–$C_2$ alkyl) quaternary ammonium salts.

Salts of primary, secondary and tertiary fatty amines are also suitable cationic surfactant materials. The alkyl groups of such amines preferably have from about 12 to about 22 carbon atoms, and may be substituted or unsubstituted. Such amines, useful herein, include stearamido propyl dimethyl amine, diethyl amino ethyl stearamide, dimethyl stearamine, dimethyl soyamine, soyamine, myristyl amine, tridecyl amine, ethyl stearylamine, N-tallowpropane diamine, ethoxylated (with 5 moles of ethylene oxide) stearylamine, dihydroxy ethyl stearylamine, and arachidylbehenylamine. Suitable amine salts include the halogen, acetate, phosphate, nitrate, citrate, lactate, and alkyl sulfate salts. Such salts include stearylamine hydrochloride, soyamine chloride, stearylamine formate, N-tallowpropane diamine dichloride, stearamidopropyl dimethylamine citrate, cetyl trimethyl ammonium chloride and dicetyl diammonium chloride. Preferred for use in the compositions herein is cetyl trimethyl ammonium chloride. Cationic amine surfactants included among those useful in the present invention are disclosed in U.S. Pat. No. 4,275,055, Nachtigal, et al., issued Jun. 23, 1981, incorporated by reference herein.

Cationic surfactants are preferably utilized at levels of from about 0.1% to about 10%, more preferably from about 0.25% to about 5%, most preferably from about 0.3% to about 0.7%, by weight of the composition.

Fatty Alcohols

The hair care compositions of the present invention may also comprise fatty alcohols. Any fatty alcohol suitable for use in hair care may be used herein. However, preferred are $C_8$ to $C_{22}$, more preferred are $C_{12}$ to $C_{18}$, even more preferred are $C_{16}$, fatty alcohols.

Fatty alcohols are preferably utilized at levels of from about 0.1% to about 20%, more preferably from about 0.25% to about 10%, most preferably from about 0.5% to about 5%, by weight of the composition.

If both fatty alcohol and cationic surfactant are present the ratio of alcohol:surfactant is preferably in the range of from about 3:1 to about 6:1, more preferably 4:1.

Water

The compositions of the present invention will also generally contain water. When present water will generally comprise from about 25% to about 99%, preferably from about 50% to about 98%, more preferably from about 65% to about 95%, by weight, of the total composition.

Additional Components

The compositions herein can contain a variety of other optional components suitable for rendering such compositions more cosmetically or aesthetically acceptable or to provide them with additional usage benefits. Such conventional optional ingredients are well-known to those skilled in the art.

A wide variety of additional ingredients can be formulated into the present composition. These include: other hair conditioning ingredients such as panthenol, panthetine, pantotheine, panthenyl ethyl ether, and combinations thereof; other solvents such as hexylene glycol; hair-hold polymers such as those described in WO-A-94/08557, herein incorporated by reference; detersive surfactants such as anionic, nonionic, amphoteric, and zwitterionic surfactants; additional viscosity modifiers and suspending agents such as xanthan gum, guar gum, hydroxyethyl cellulose, triethanolamine, methyl cellulose, starch and starch derivatives; viscosity modifiers such as methanolamides of long chain fatty acids such as cocomonoethanol amide; crystalline suspending agents; pearlescent aids such as ethylene glycol distearate; opacifiers such as polystyrene; preservatives such as phenoxyethanol, benzyl alcohol, methyl paraben, propyl paraben, imidazolidinyl urea and the hydantoins; polyvinyl alcohol; ethyl alcohol; pH adjusting agents, such as lactic acid, citric acid, sodium citrate, succinic acid, phosphoric acid, sodium hydroxide, sodium carbonate; salts, in general, such as potassium acetate and sodium chloride; colouring agents, such as any of the FD&C or D&C dyes; hair oxidising (bleaching) agents, such as hydrogen peroxide, perborate and persulfate salts; hair reducing agents, such as the thioglycolates; perfumes; sequestering agents, such as tetrasodium ethylenediamine tetra-acetate; anti-dandruff agents such as zinc pyrithione (ZPT), sulfur, selenium sulfide, coal tar, piroctone olamine, ketoconazole, climbazole, salicylic acid; antioxidants/ultra violet filtering agents such as octyl methoxycinnamate, benzophenone-3 and DL-alpha tocopherol acetate and polymer plasticizing agents, such as glycerine, diisobutyl adipate, butyl stearate, and propylene glycol. Such optional ingredients generally are used individually at levels from about 0.001% to about 10.0%, preferably from about 0.01% to about 5.0% by weight of the composition.

Product Forms

The hair care compositions of the present invention can be formulated in a wide variety of product forms, including but not limited to creams, gels, aerosol or non-aerosol foams, mousses and sprays. Mousses, foams and sprays can be formulated with propellants such as propane, butane, pentane, dimethylether, hydrofluorocarbon, $CO_2$, $N_2O$, or without specifically added propellants (using air as the propellant in a pump spray or pump foamer package).

Method of Use

The hair care compositions of the present invention may be used in a conventional manner for care of human hair. An effective amount of the composition, typically from about 1 gram to about 50 grams, preferably from about 1 gram to about 20 grams, is applied to the hair. Application of the composition typically includes working the composition through the hair, generally with the hands and fingers, or with a suitable implement such as a comb or brush, to ensure good coverage. The composition is then left on the hair, generally until the consumer next washes their hair.

The preferred method of treating the hair therefore comprises the steps of:

(a) applying an effective amount of the hair care composition to wet, damp or dry hair, (b) working the hair care composition into the hair with hands and fingers or with a suitable implement.

The method can, optionally, comprise a further step of rinsing the hair with water.

EXAMPLES

The following examples further illustrate the preferred embodiments within the scope of the present invention. The examples are given solely for the purposes of illustration and are not to be construed as limitations of the present invention as many variations of the invention are possible without departing from its spirit or scope. All ingredients are expressed on a weight percentage of the active ingredient.

Examples I (% wt)

| | I (Spray) |
|---|---|
| Water | qs |
| Cationic Polymer of hydroxyethyl cellulose[1] | 0.075 |
| trisodium citrate | 0.70 |
| PEG 60 hydrogenated castor oil[2] | 0.80 |
| lactic acid | 0.10 |
| phenoxyethanol | 0.20 |
| CI 42045 (Acid blue 1) | 0.0001 |
| Perfume | 0.10 |

[1]Polymer having a charge density of 1.93 meq/g and wt average mol. wt of 1.25 million. Available from Amerchol.
[2]Cremaphor RH-60 supplied by BASF The cationic polymer and the trisodium citrate are added to water and stirred thoroughly at ambient conditions until a homogenous solution is obtained. All the other ingredients are then mixed together and added to the homogenous solution. The resulting solution is then stirred until homogenous.

Example II (% wt)

| | II (Mousse) |
|---|---|
| Water | qs |
| Cationic Polymer of hydroxyethyl cellulose[1] | 0.30 |
| trisodium citrate | 0.10 |
| PEG 60 hydrogenated castor oil[2] | 0.10 |
| CAPB[3] | 0.30 |
| lactic acid | 0.02 |
| phenoxyethanol | 0.30 |
| Perfume | 0.25 |

[1]Polymer having a charge density of 1.93 meq/g and wt average mol. wt of 1.25 million. Available from Amerchol.
[2]Cremaphor RH-60 supplied by BASF
[3]Tegobetaine F supplied by Goldschmidt The cationic polymer and the trisodium citrate are added to water and stirred thoroughly at ambient conditions until a homogenous solution is obtained. All the other ingredients are then mixed together and added to the homogenous solution. The resulting solution is then stirred until homogenous. The resulting product is then packaged in a pressurised aerosol container with volatile propellant (propane, butane, etc.) at a fill ratio 10–15 parts concentrate to 1 part propellant.

Examples III–IV (% wt)

|  | III (Cream) | IV (Cream) |  |
|---|---|---|---|
| Water | qs | qs | — |
| Carbomer[1] | 1.00 | — | A |
| Acrylates/C10–30 alkyl acrylate cross polymer[2] | — | 0.60 | A |
| Cationic Polymer of hydroxyethyl cellulose[11] | 1.00 | 0.10 | B |
| methyl parabens | 0.08 | — | C |
| propyl parabens | 0.04 | — | C |
| Cetyl alcohol[3] | 2.40 | 1.00 | C |
| Stearyl alcohol | — | 0.50 | C |
| Cetrimmonium chloride[4] | 0.60 | — | C |
| PEG 60 hydrogenated castor oil[5] | 0.05 | — | C |
| Ammonium Lauryl Sulphate[6] | 0.10 | — | C |
| PEG100 stearate[7] | — | 0.13 | C |
| Ethanol (denatured) | — | 30.00 | D |
| Camphor | 0.10 | — | D |
| I-isopulegol[8] | — | 0.50 | D |
| Polyquaternium 4[9] | 0.10 | — | D |
| 2-phenylpropyl M'Q resin[10] | — | 0.50 | D |
| lactic acid | — | 0.15 | D |
| phenoxyethanol | 0.20 | 0.20 | D |
| tetra sodium EDTA | 0.01 | — | D |
| citric acid | 0.10 | — | D |
| Perfume | 0.60 | 1.00 | D |
| Triethanolamine | 0.40 | 0.40 | E |

[1]Carbopol Ultrez 10 supplied by BF Goodrich)
[2]Pemulen TR2 supplied by BF Goodrich
[3]Crodacol C-95 supplied by Croda Inc.
[4]Dehyquat A supplied by Henkel
[5]Cremophor RH-60 supplied by BASF.
[6]Empicol AL 30/T supplied by Albright & Wilson
[7]Myrj 59 supplied by ICI Surfactants
[8]Coolact P supplied by Takasago
[9]Celquat L200 supplied by National Starch
[10]Prepared according to GB-A-2,297,775
[11]Polymer having charge density of 1.93 meq/g and wt average mol. wt of 1.25 million. Available from Amerchol.

Ingredients A are solubilized in water and then heated to 80° C. All of ingredients C are then added and the resulting mixture cooled by recirculation to 30° C. through a plate heat exchanger with simultaneous high shear mixing. Batch Cooling rate is maintained at between 1.0 and 1.5° C./min. All of ingredients D are then added and 50% of ingredient E, the triethanolamine. This mixture is then stirred until homogenous. Ingredient B is then solubilized in water and added to the main mix. This mixture is then subjected to high shear mixing until homogenous particle size distribution is achieved. Recirculation is then stopped to prevent shear stress damage to product during completion of neutralisation.

The remaining ingredient E, triethanolamine, is added until the specified pH and viscosity is achieved.

Example V (% wt)

| | V (Lotion) | |
|---|---|---|
| Water | qs | — |
| methyl parabens | 0.50 | A |
| propyl parabens | 0.40 | A |
| Cetyl alcohol[1] | 1.60 | A |
| Cetrimmonium chloride[2] | 0.40 | A |
| PEG 60 hydrogenated castor oil[3] | 0.10 | A |
| Cationic Polymer of hydroxyethyl cellulose[5] | 0.20 | B |
| Dimethicone[4] | 0.20 | C |
| Styryl M'Q resin | 0.20 | C |
| zinc pyrithione | 0.03 | C |
| octyl methoxycinnamate | 0.10 | C |
| benzophenone-3 | 0.02 | C |
| DL-alpha tocopherol acetate | 0.03 | C |
| DMDM hydantoin | 0.05 | C |
| tetra sodium EDTA | 0.30 | C |
| citric acid | 0.20 | C |
| Perfume | 0.40 | C |

[1]Crodacol C-95 supplied by Croda Inc.
[2]Dehyquat A supplied by Henkel
[3]Cremophor RH-60 supplied by BASF
[4]DC200 supplied by Dow Corning
[5]Polymer having charge density of 1.93 meq/g and wt average mol. Wt of 1.25 million. Available from Amerchol.

Ingredients A are solubilized in water and then heated to 80° C. The resulting mixture cooled to 30° C. through a plate heat exchanger with simultaneous high shear mixing. The cooling rate is maintained at between 1.0 and 1.5° C./min. All of ingredients C are then added. This mixture is then stirred until homogenous. Ingredient B is then solubilized in water and added to the main mix. This mixture is then subjected to high shear mixing until homogenous particle size distribution is achieved.

What is claimed is:

1. A hair care composition comprising:
   a) cationic polymers and/or copolymers of saccharides wherein the cationic saccharide has a charge density of greater than about 1.5 meq/g; and
   b) less than about 5%, by weight, of an anionic surfactant.

2. A hair care composition according to claim 1 wherein the cationic saccharide has a charge density less than about 5 meq/g.

3. A hair care composition according to claim 1 or 2 wherein the composition is a 'leave-on' conditioner.

4. A hair care composition according to any one of the preceding wherein the cationic saccharide has an average molecular weight of from about 5000 to about 10 million.

5. A hair care composition according to any one of the preceding claims wherein the cationic saccharide is selected from cationic polymers and copolymers of cellulose derivatives.

6. A hair care composition according to any one of the preceding claims wherein the cationic saccharide is a cationic polymer of hydroxyethylcellulose.

7. A hair care composition according to any one of the preceding claims wherein the cationic saccharide comprises from about 1% to about 10%, by weight, of cationic nitrogen.

8. A hair care composition according to any one of the preceding claims wherein the cationic saccharide comprises from about 0.001% to about 20%, by weight, of the total composition.

9. A hair composition according to any one of the preceding claims wherein the composition further comprises a silicone conditioning compound.

10. A hair care composition according to claim 9 wherein the silicone conditioning agent is an aryl, alkaryl or arylalkyl modified silicone.

11. A hair care composition according to claim 9 or 10 wherein the silicone conditioning agent is a resin.

12. A hair care composition according to claim 11 wherein the silicone resin has a viscosity of less than about 5000 $mm^2s^{-1}$.

13. A hair care composition according to any one of the preceding claims wherein the composition further comprises a $C_1$ to $C_6$ aliphatic alcohol.

14. A method of conditioning hair by applying to the hair an effective amount of a composition according to any one of the preceding claims.

15. A hair care composition comprising:
   a) cationic polymers and/or copolymers of saccharides wherein the cationic saccharide has a charge density of greater than about 1.8 meq/g; and
   b) less than about 2%, by weight, of an anionic surfactant.

16. A hair care composition comprising;
   a) cationic polymers and/or copolymers of saccharides wherein the cationic saccharide has a charge density of greater than about 1.8 meq/g; and
   b) less than about 0%, by weight, of an anionic surfactant.

17. A hair care composition according to claim 1 wherein the cationic saccharide has a charge density of less than about 3.5 meq/g.

18. A hair care composition according to claim 1 wherein the cationic saccharide has a charge density of less than about 2.2 meq/g.

19. A hair care composition according to any one of the preceding wherein the cationic saccharide has an average molecular weight of from about 1 million to about 1.5 million.

20. A hair care composition according to any one of the preceding claims wherein the cationic saccharide comprises from about 2.5% to about 2.9%, by weight, of cationic nitrogen.

21. A hair care composition according to any one of the preceding claims wherein the cationic saccharide comprises from about 0.01% to about 2%, by weight, of the total composition.

22. A hair care composition according to any one of the preceding claims wherein the cationic saccharide comprises from about 0.05% to about 1%, by weight, of the total composition.

23. A hair care composition according to claim 10 wherein the silicone conditioning agent is an arylalkyl modified silicone.

24. A hair care composition according to claim 9 wherein the silicone resin has a viscosity of less than about 1000 $mm^2s^{-1}$.

25. A hair care composition according to claim 24 wherein the silicone resin has a viscosity of less than about 600 $mm^2s^{-1}$.

26. A hair care composition according to any one of the preceding claims wherein the composition further comprises $C_2$ aliphatic alcohol.

* * * * *